(12) United States Patent  
Pond

(10) Patent No.: US 10,258,494 B2  
(45) Date of Patent: Apr. 16, 2019

(54) TREATMENT OF SPINAL DEFORMITIES

(71) Applicant: Tyler Pond, Nampa, ID (US)

(72) Inventor: Tyler Pond, Nampa, ID (US)

( * ) Notice: Subject to any disclaimer, the term of this patent is extended or adjusted under 35 U.S.C. 154(b) by 548 days.

(21) Appl. No.: 14/956,341

(22) Filed: Dec. 1, 2015

(65) Prior Publication Data

US 2016/0151191 A1 Jun. 2, 2016

Related U.S. Application Data

(60) Provisional application No. 62/085,656, filed on Dec. 1, 2014.

(51) Int. Cl.
*A61F 5/02* (2006.01)

(52) U.S. Cl.
CPC .............. *A61F 5/024* (2013.01); *A61F 5/026* (2013.01)

(58) Field of Classification Search
CPC .......... A61F 5/024; A61F 5/026; A61F 5/028; A61F 5/03; A61F 13/14
See application file for complete search history.

(56) References Cited

U.S. PATENT DOCUMENTS

| | | | | |
|---|---|---|---|---|
| 888,490 A | * | 5/1908 | Haas | A61F 5/028 602/19 |
| 5,163,450 A | * | 11/1992 | Cadichon | A61F 5/3723 128/869 |
| 6,464,656 B1 | * | 10/2002 | Salvucci | A61F 5/3738 602/20 |
| 7,842,000 B2 | * | 11/2010 | Lai | A61F 5/026 602/19 |
| 2013/0245522 A1 | | 9/2013 | Modglin | |
| 2014/0276308 A1 | * | 9/2014 | DiAngelo | A61F 5/02 602/19 |
| 2014/0330187 A1 | * | 11/2014 | Perez | A61F 5/028 602/19 |

OTHER PUBLICATIONS

Spinal Technology, Inc.; Product Catalog; date unknown; available at http://www.spinaltech.com/catalog/files/assets/downloads/Spinal%20Technology%20Product%20Catalog.pdf (last accessed Nov. 10, 2016).
SpineCor; The SpineCor Dynamic Corrective Brace; Mar. 18, 2013; available at https://issuu.com/creativefive/docs/spine_corporation_brochure_2010-12pg (last accessed Nov. 10, 2016).

* cited by examiner

*Primary Examiner* — Ophelia A Hawthorne
(74) *Attorney, Agent, or Firm* — Scott D. Swanson; Shaver & Swanson, LLP

(57) ABSTRACT

Treatment of a spinal lateral translation may be carried out by tensioning a cable that is set around a subject at the approximate height of the lateral translation. A tensioner may tension the cable, thereby directing a lateral corrective force from one or more anchor points toward the spinal deformity. Tension may be applied to the cable by a tensioning assembly such as one having a ratcheting device. A frame can maintain the anchor point(s), cable(s), and tensioning assembly(ies) at desired vertical and/or lateral positions. A device comprising the foregoing components may be wearable by the subject.

10 Claims, 7 Drawing Sheets

TREATMENT OF SPINAL DEFORMITIES

CROSS-REFERENCE TO RELATED APPLICATIONS

This application claims the benefit of U.S. Provisional Patent Application Ser. No. 62/085,656, filed Dec. 1, 2014, and titled "TREATMENT OF SPINAL DEFORMITIES," the entire contents of which are hereby incorporated herein by reference.

BACKGROUND

Technical Field

The present disclosure relates generally to treatment of spinal deformities in a subject. In particular, the present disclosure relates to apparatus, methods, and systems for treating and/or aligning lateral translations in a subject, including but not limited to scoliosis or other deviations in a subject's spine.

Description of Related Art

Spinal deformities may be caused by congenital factors, neuromuscular disease, or by other factors. A spinal lateral translation may result in undesirable symptoms and complications, such as muscular fatigue, chronic pain in the shoulder, neck and/or back, nerve pinching, affected physical appearance, lung damage, and heart damage.

Scoliosis is generally defined as a spinal lateral translation having a Cobb angle of more than ten degrees. However, even subjects having lateral translations with a Cobb angle of 10 degrees or less may suffer from the foregoing symptoms or complications.

Current treatment methods for spinal deformities include various braces. In general, braces are understood to be essentially ineffective as a corrective measure, but may be used to prevent further progression of deformities of the spine.

In some treatments, the subject is put into skeletal traction in an attempt to correct a spinal deformity. For example, a subject may be strapped into a harness having anchor points on a separate structure beside the subject. The anchor points are typically mounted to a wall or other structure. The harness is tightened to apply lateral forces at the spinal deformities of the subject. A traction treatment session may typically last 20-30 minutes. Sessions may be repeated on a regular basis.

BRIEF DESCRIPTION OF THE FIGURES

Non-limiting and non-exhaustive embodiments of the present disclosure are described with reference to the following figures, wherein like reference numerals refer to like parts throughout the various views unless otherwise specified.

DETAILED DESCRIPTION

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the spirit and scope of the present disclosure. The following detailed description is, therefore, not to be taken in a limiting sense.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples. In addition, it should be appreciated that the figures provided herewith are for explanation purposes to persons ordinarily skilled in the art and that the drawings are not necessarily drawn to scale.

Figure 1:
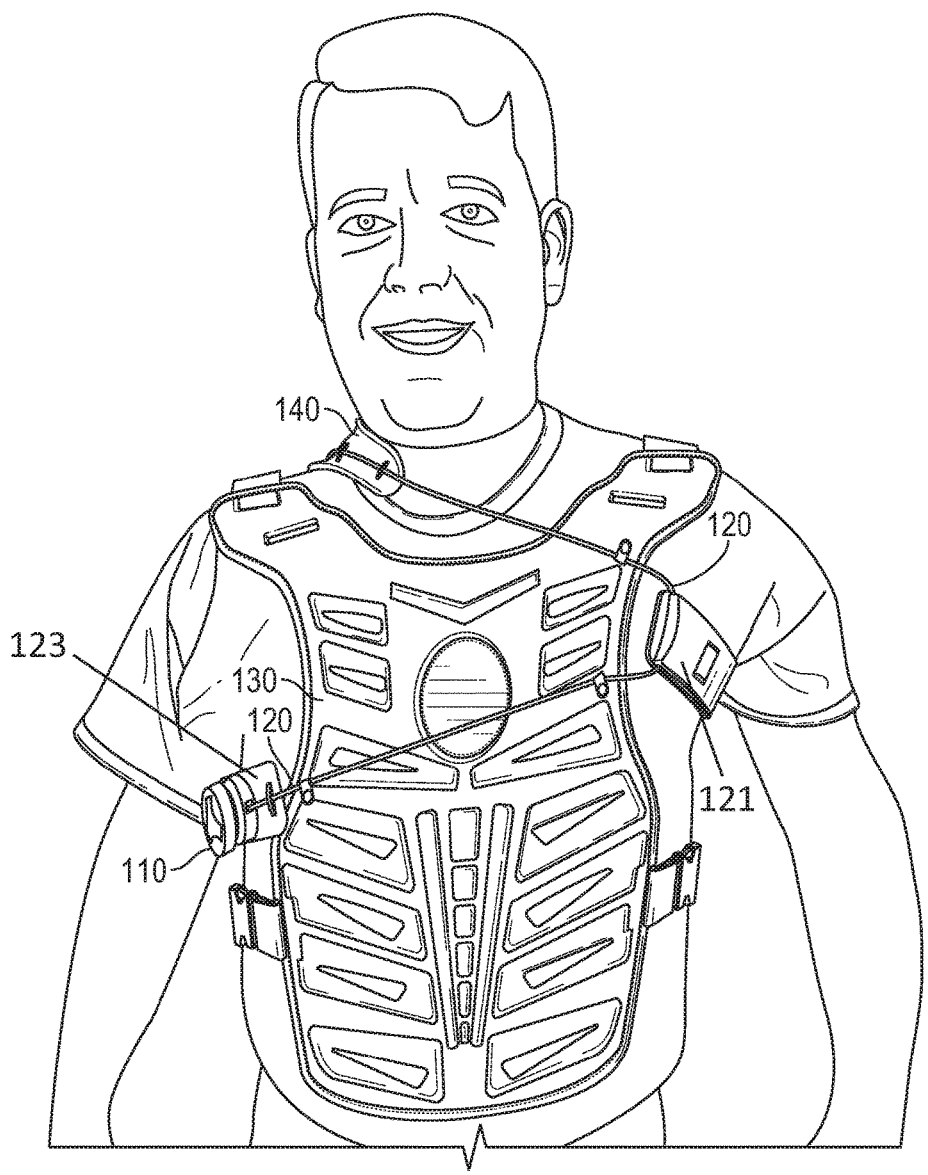
FIG. 1 depicts a front view of spinal deformity treatment device according to an embodiment of the present disclosure.
Figure 2:
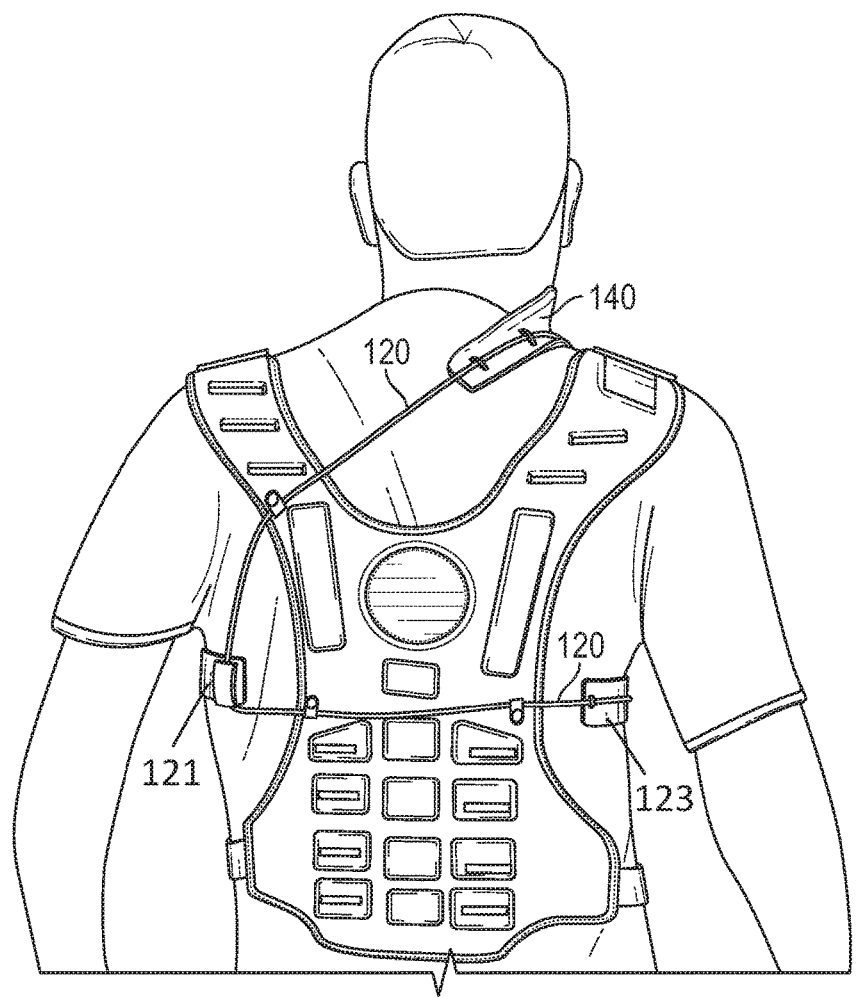
FIG. 2 depicts a rear view of spinal deformity treatment device according to an embodiment of the present disclosure.

Embodiments of the present disclosure comprise a system 100 for applying lateral forces to spinal deformities. Referring to FIGS. 1 and 2, one embodiment of the present disclosure comprises tensioners 110, cables 120, frame 130, and neck piece 140. In one embodiment, tensioners 110 comprise assemblies adapted to tension cables 120. In one embodiment, tensioners 110 comprises internal winding mechanisms. In one embodiment, tensioner 110 comprises a ratcheting mechanism to maintain tension at a selected tension level. In other embodiments, tensioners comprise electric motors adapted to create and sustain a selected tension on cables 120. Other embodiments comprise combinations of the foregoing components. The term "tensioning assembly" may refer to any type of mechanism, assembly, or component that can create and/or maintain a tension on a cable 120, strap, rope, or other tensionable member.

Each tensioner 110 represents an anchor point to apply lateral forces to the subject's spine. In an embodiment, tensioner 110 applies essentially equal pulling forces to two cables 120, one passing around the front of the subject and another passing around the back of the subject, and joining at another anchor point. In various embodiments, anchor points comprise tensioners 110, neck member 140, or other like points. In embodiments, loops may be formed by cable segments passing in front of and behind the subject and join at anchor points. As each tensioner 110 is tightened, the loop constricts, thereby applying lateral forces at each anchor point in the loop.

In embodiments, the ratcheting mechanism of tensioner 110 comprises small enough steps that the subject can precisely select a desired tension with relatively little backlash. For example, in one embodiment, the ratcheting mechanism comprises 20 teeth or more. Another embodiment comprises at least 40 teeth in the ratchet mechanism. Another embodiment comprises at least 60 teeth in the ratchet mechanism. In other embodiments, ratcheting mechanism comprises a toothless ratchet mechanism.

In one embodiment, numbers are printed on the body of the tensioner that indicate the degree to which the ratchet (or other tension device) has currently rotated. For example, a dial pointer may correspond to rotation of the ratchet gear, such that as the gear is rotated relative to the body, the dial pointer points to the corresponding number. Each number may represent an arbitrary degree of rotation. In this manner, a subject may set each tensioner at the desired tension. By recording the tensioner setting over time, the subject may track progress by observing rotation increases of the tensioner.

One embodiment of the present disclosure comprises a single tensioner. In this exemplary embodiment, cables slide through a cable housing or pulley, wrap around a hook, or pass through and/or around other cable management components. In one embodiment, cables pass through groves on the frame that position cable placement. The single tensioner may thus be used to apply tension to the entire length of cable. In this embodiment, each cable management component comprises an anchor point that, when tension is applied to the cable or other tensionable member, applies a lateral force to the subject.

In one embodiment having a single tensioner, one or more anchor points comprise a cable locking component capable of isolating segments of the cable, such that individually-selected tensions for each respective segment may be applied. In such an embodiment, tension for the length of cable farthest from the tensioner may first be dialed in at the tensioner. The locking component that isolates that length of cable may then be activated, thus locking in the desired tension setting of the length of cable. The remaining cable may then be set at the selected tension setting for the next length of cable by decreasing tension, increasing tension, or leaving the setting the same at the tensioner. The brake component that isolates the second segment may then be activated, thereby locking in the tension of the second length of cable. Each segment of cable may thus be individually tensioned at a desired tension setting using only a single tensioner.

As depicted in FIG. 1, cables 120 are wound inside each tensioner to apply lateral force at each anchor point. In one embodiment, cables 120 comprise compliant, non-elastic lengths of various materials. In embodiments, cables 120 are manufactured from nylon or other polymer line, nylon webbing or other types of straps, braided or non-braided metal wire line, or other flexible lengths. In other embodiments, a rigid or semi-rigid member is used as the tensionable member between each anchor point.

In alternative embodiments, a tensioning assembly and a tensionable member are combined into a single component. For example, an elastic tensionable length is stretched between anchor points to apply tension between them. Selected lengths of appropriate elasticity and strength may result in a desired tension for the subject.

Embodiments comprise frame 130. One embodiment of frame 130 comprises mounting locations for anchor points and/or tensioners. In the embodiment depicted in FIG. 2, frame 130 comprises a front plate. In other embodiments, the frame comprises a back plate. In other embodiments, the frame comprises side plates. In some embodiments, each one of the front plate, side plates, and/or back plate comprises multiple constituent rigid components. According to various embodiments, the frame comprises over-the-shoulder straps that connect a front, side, and/or back plate together. Embodiments of frame may be held in place by a combination of gravity and tension on cables 120. In one embodiment, the frame has the appearance and/or shape of a vest.

Embodiments comprise one or more vertically-spaced lines of slots on the frame into which cables 120 may be positioned. The slots can hold cables 120 in place and resist the tendency of cables 120 to slide up or down. For example, referring to FIG. 1, tensioners 110 are not vertically level with each other. According to embodiments, tensioners 110 may be placed at the height of each lateral translation of the subject's spine such that when cables 120 are tensioned, a corrective force is applied to the curvature. The height difference between tensioners 110 may cause cables 120 and/or tensioners 110 to slide up or down and therefore out of the designated position. Accordingly, slots on frame 130 can maintain cables 120 and tensioners 110 in a desired position by selecting the slot of appropriate height and inserting a portion of cable 120 therein. One embodiment of the frame comprises a slot cover that is adapted to slide into place, covering the slots and reducing the likelihood that cable 120 will be pulled out of the slot into which it was placed. Embodiments of the present disclosure comprise slots at various positions on frame 130 on the front, sides, and/or rear of frame 130 or any positions therebetween.

Embodiments of the frame 130 comprise hard surfaces for distributing the lateral forces from the anchor points and/or cables across a wider area of the subject's body to reduce discomfort. Tensioned cables could potentially dig into the subject's skin, causing discomfort and potentially discouraging prolonged use of system 100 to the detriment of the subject. According to various embodiments, frame 130 allows tensioners 110 or other types of anchor points to be mounted to either side of the subject's body at any selected height along the subject's torso, as shown by side anchor points 121, 123.

One embodiment of neck piece 140 comprises a rigid, curved anchor point attached to cables 120. In one embodiment, neck piece 140 is adapted to contact the subject at a portion of the upper trapezius muscle, such that the neck piece is positioned generally where a subject's neck and trapezius muscle meet as shown for example in FIGS. 1, 2, 3, 6, 7, and 8. The shape of neck piece 140 may be made to conform to a particular subject or may comprise a shape that generally fits subjects of various sizes and body types. When the cables 120 are tensioned, neck piece acts as an anchor point and transfers a lateral force to the subject's neck.

In operation, devices for the treatment of spinal deformities according to the present disclosure may be worn by a subject to correct said spinal deformities. The device can be used in repeated sessions in a corrective regimen. In embodiments, such treatment sessions may be carried out at the direction of a medical professional.

Figure 3:
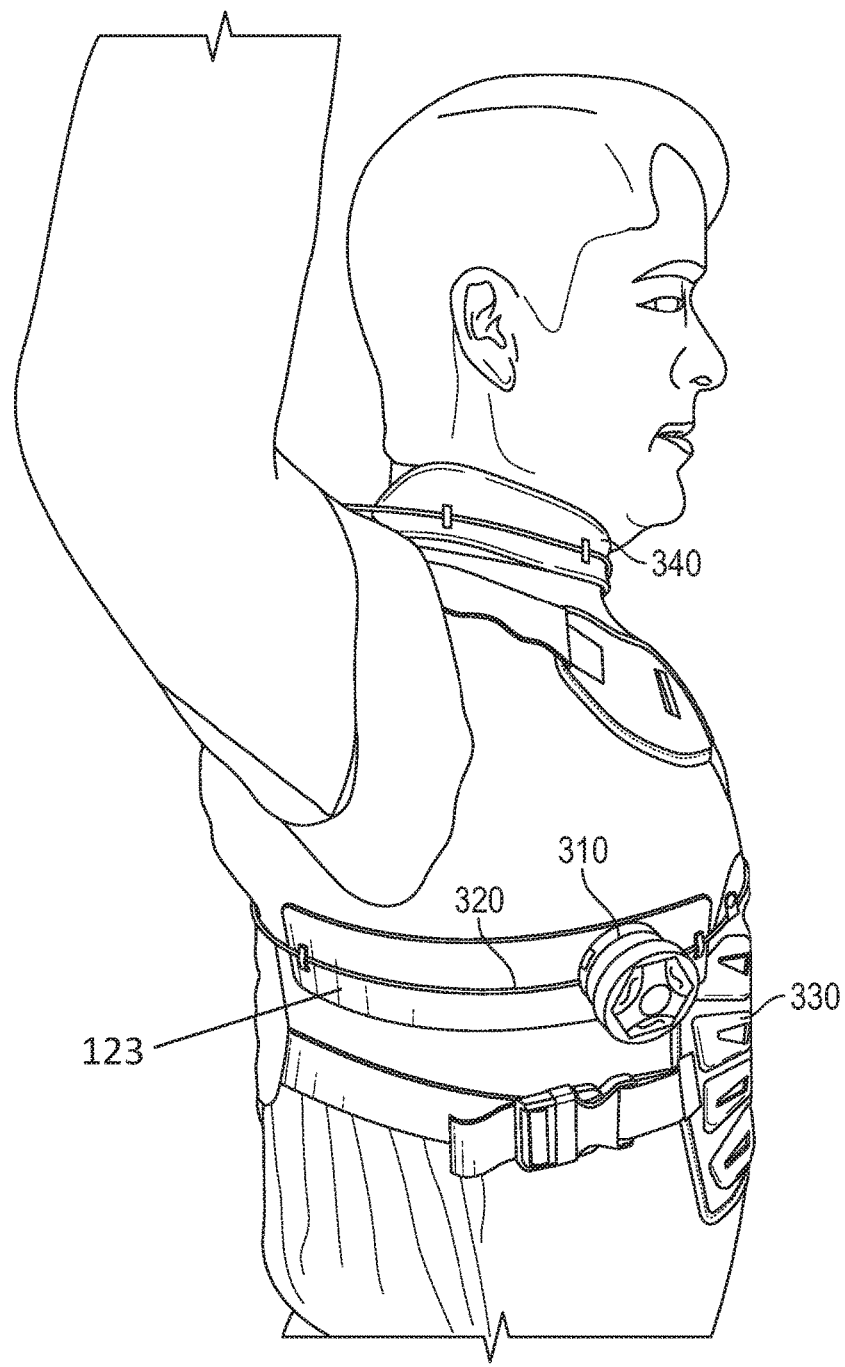
FIG. 3 depicts a right side view of spinal deformity treatment device according to an embodiment of the present disclosure.
Figure 4:
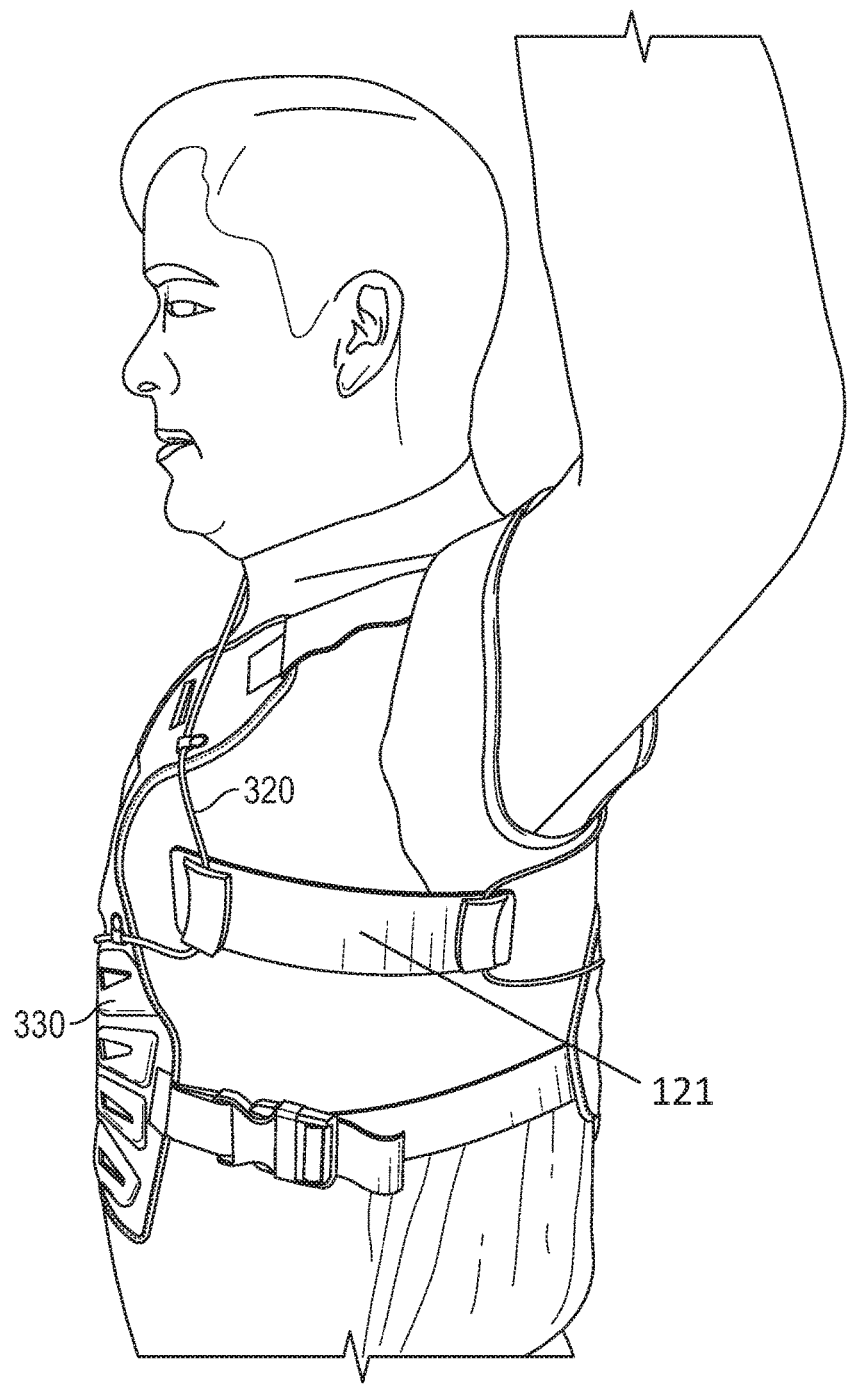
FIG. 4 depicts a left side view of spinal deformity treatment device according to an embodiment of the present disclosure.
Figure 5:
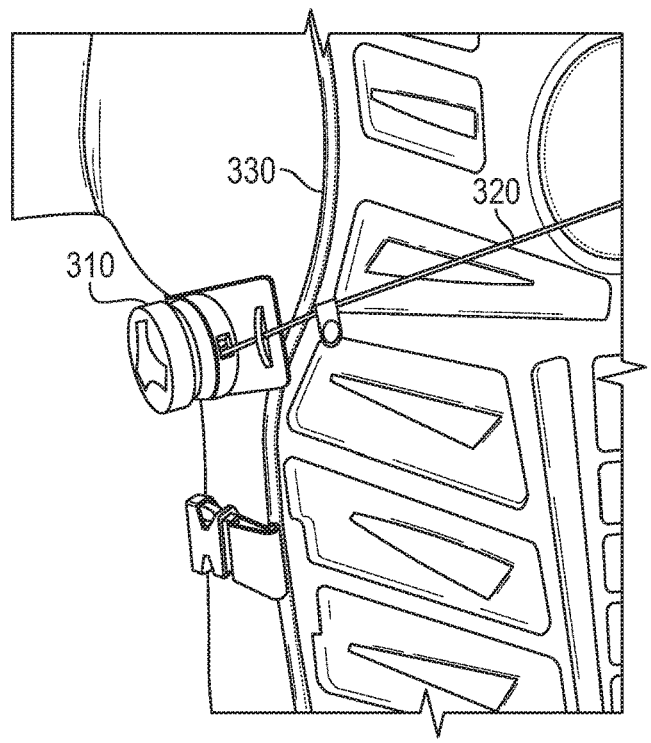
FIG. 5 depicts a tensioning assembly according to an embodiment of the present disclosure.
Figure 6:
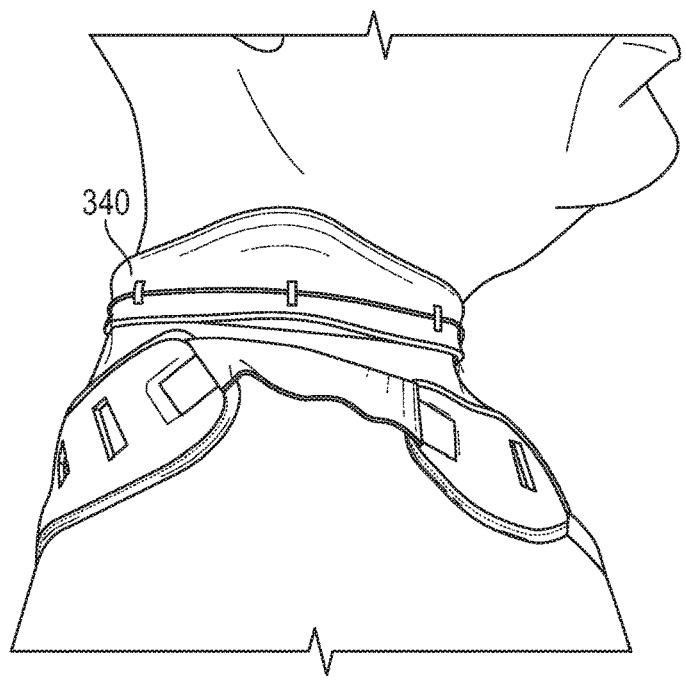
FIG. 6 depicts a side view of a neck piece of spinal deformity treatment device according to an embodiment of the present disclosure.
Figure 7:
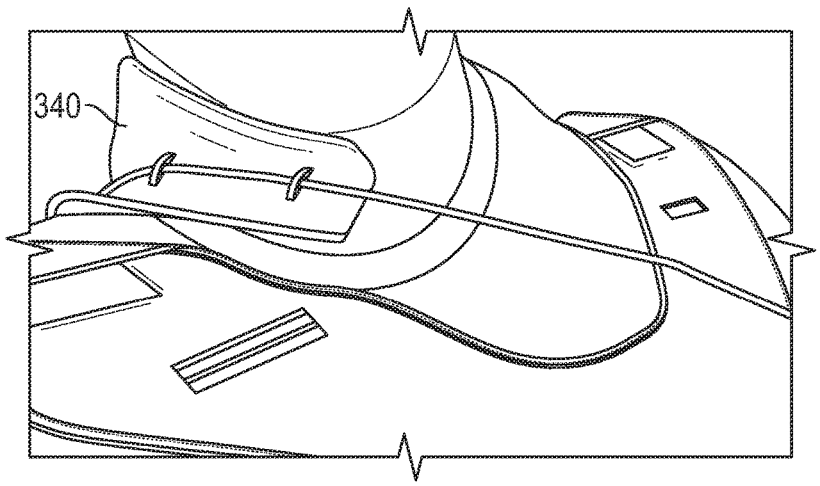
FIG. 7 depicts a front view of a neck piece of spinal deformity treatment device according to an embodiment of the present disclosure.
Figure 8:
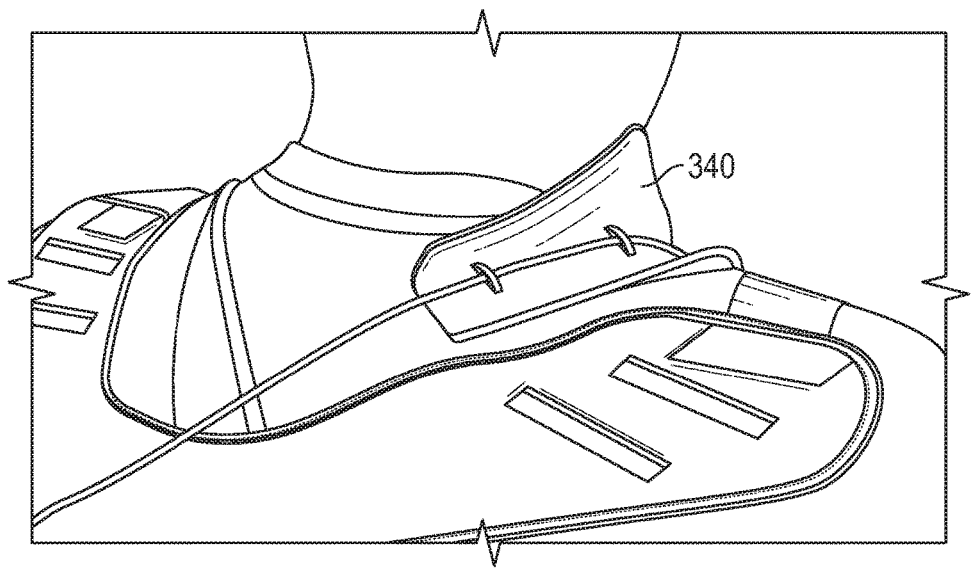
FIG. 8 depicts a rear view of a neck piece according to an embodiment of the present disclosure.

Referring now to FIGS. 3-5, to put on the device, frame 330 can first be put on the subject. Tensioners 310 can be placed at the subject's sides at the approximate height of one or more lateral translations of the subject's spine. Referring to FIGS. 6-8, if the subject has a spinal lateral translation at the cervical vertebrae and/or upper thoracic vertebrae, neck piece 340 may be placed at the subject's neck. In an embodiment, the tensioners are connected to each other and any other anchor points by cables, straps, or other types of tensionable members. According to one embodiment, tensioners 310 can each be vertically positioned at virtually any point on the side of the subject's torso from the waist to the armpit. Cables 320 may be slightly tensioned to hold tensioners 310 in place during positioning of other components. When components are in their desired positions, tensioners 310 may be used to apply tension to cables 320 until a desired tension level is reached.

Because the treatment device is worn on the subject's body, it may be used essentially at almost any time and nearly on a continuous basis. Near-constant use of the treatment device may increase the effectiveness of such treatments. Over time, as a subject makes progress with treatments, it may be desirable to increase the lateral displacement of each anchor point. Thus, in one embodiment, the subject can turn each tensioner to a farther position than had previously been used.

It may be advantageous to set and tension the cables while the subject is observed through an X-ray device to observe spinal alignment and optimize the tension settings. In one embodiment, a subject may wear tensioners and cable without the frame while in front of an X-ray device. In another embodiment, the frame has an open front, such that X-rays are not blocked while the frame is worn by the subject. Each cable can be tensioned while a medical professional observes the effects on the spinal lateral translations as depicted by the x-ray device. Each cable may be tensioned in turn to determine optimal tension settings, which the subject may repeat in subsequent treatment sessions.

In one embodiment, the frame comprises one or more vibration components to massage the subject when activated. In various embodiments, a vibration component is positioned at the subject's chest area. In some embodiments, a vibration component is placed at the subject's back. Multiple vibration components may be installed on the frame. In some embodiments, the rigid members of the frame transmit the vibrations to the subject. The vibration component(s) may be activated to relax the subject's muscles, to increase subject comfort, and/or to increase effectiveness of the treatment device.

In one embodiment, the vibration component is powered by a battery connected to frame 130 or otherwise carried by the subject. In other embodiments, the vibration component is powered by an electrical outlet or other power source. In one embodiment, the vibration component(s) include an internal oscillating unbalanced weight.

Figure 9:
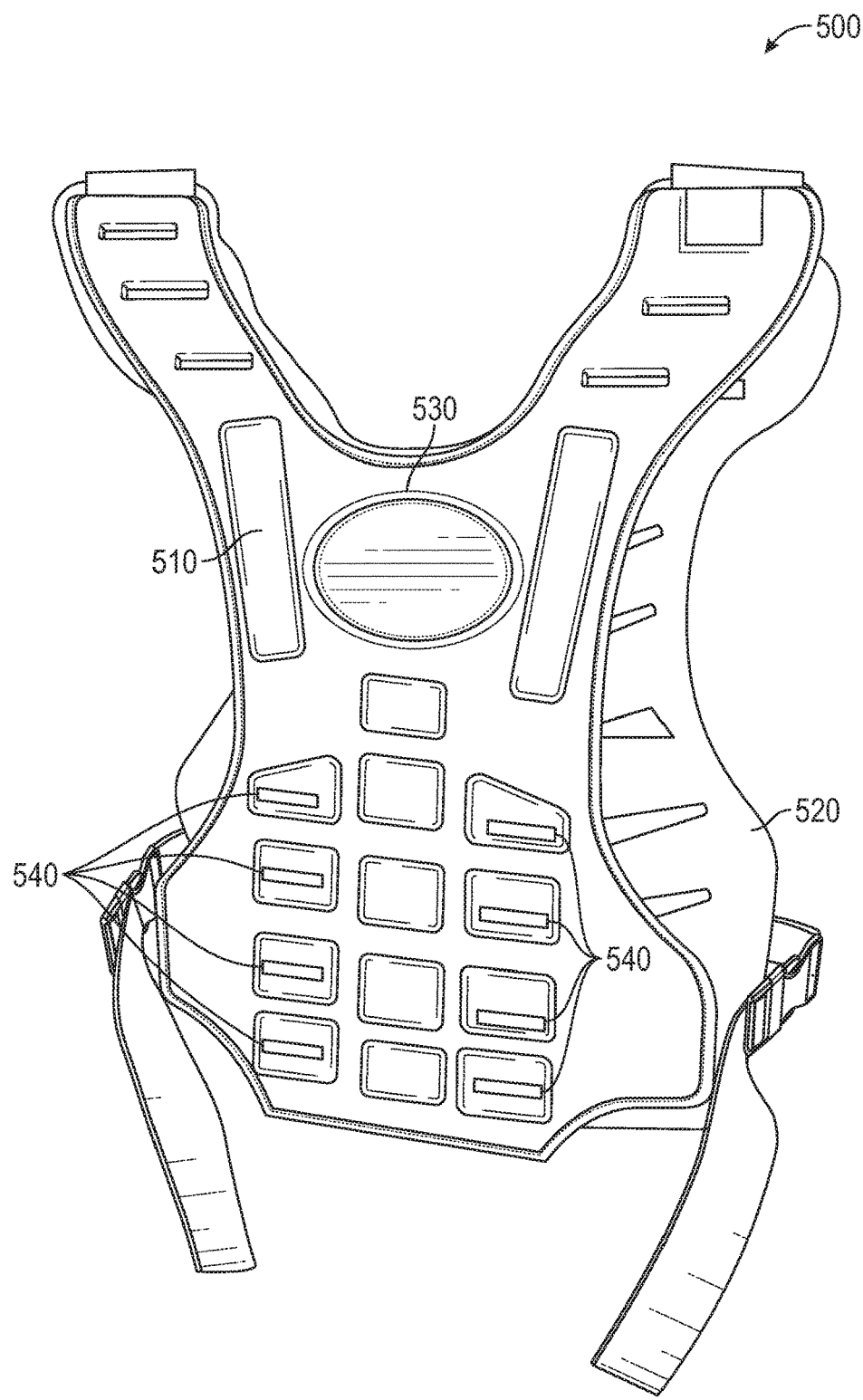
FIG. 9 depicts a spinal deformity treatment device having a vibration component according to an embodiment of the present disclosure; and Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

Referring to FIG. 9, an illustration of a frame 500 according to one embodiment is provided showing a front frame portion 510 and a rear frame portion 520. Vibration component 530 may be positioned at the subject's chest and back (not pictured). Slots 540 can maintain proper positioning of cables and anchor points.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the spirit and scope of the present disclosure.

What is claimed is:

1. A spinal deformity treatment device, comprising:
a frame adapted to be worn on a subject's torso;
a tensionable member comprising a first end and a second end, wherein said tensionable member is attached to a tensioner member, wherein said tensionable member is slideably attached to said frame, wherein said tensionable member forms an endless loop;
wherein said tensioner member comprises an internal winding mechanism;
wherein said tensionable member is configured to form a loop around a subject's torso generally where the subject's neck and trapezius muscle meet;
wherein from said loop a first segment of said tensionable member is configured to traverse the ventral side of a subject's torso, wherein a second segment of said tensionable member is configured to traverse the dorsal side of a subject's torso, wherein said tensionable member is configured to form a first lateral side loop around a subject's first lateral side inferior to a subject's first arm;
wherein a third segment of said tensionable member is configured to traverse the dorsal side of a subject's torso from said first lateral side loop and a fourth segment of said tensionable member is configured to traverse the ventral side of a subject's torso from said first lateral side loop, wherein said third segment and said forth segment are configured to meet to form a second lateral side loop around the subject's body at an opposite lateral side of said subject's body from said first lateral side loop, wherein said tensionable member is configured to apply lateral force to said subject's body at each of said loops, wherein said tensioner member is configured to adjust the lateral force applied by said tensionable member by applying tension to said tensionable member.

2. The spinal deformity treatment device of claim 1, further comprising a neck member, wherein said neck member is configured to form a rigid loop around said subject's torso proximate to where said subject's neck and trapezius muscle meet, wherein said neck member is configured such that said tensionable member applies force to said neck member to apply force to said subject's torso.

3. The spinal deformity treatment device of claim 2, wherein said neck member is attached to said tensionable member and configured to form said loop around a subject's neck.

4. The spinal deformity treatment device of claim 1, wherein said device comprises a second side anchor point, wherein said second side anchor point comprises a curved rigid length, wherein said second side anchor point is configured to form a loop around said subject's body on the same lateral side of said subject's body as said loop around a subject's torso generally where the subject's neck and trapezius muscle meet.

5. The spinal deformity treatment device of claim 4, wherein said tensioner member is attached to said second side anchor point.

6. The spinal deformity treatment device of claim 1, wherein said tensionable member comprises a cable.

7. The spinal deformity treatment device of claim 1, wherein said tensionable member comprises an elastic tensionable member.

8. The spinal deformity treatment device of claim 1, wherein said tensionable member comprises a first side anchor point, wherein said first side anchor point comprises a curved length having a first end and a second end, wherein said first end is connected to said first segment of said tensionable member, wherein said second end is connected to said second segment of said tensionable member, wherein said first anchor point forms said first loop around said subject's torso.

9. A spinal deformity treatment device, comprising:
a frame adapted to be worn on a subject's torso;
a tensionable member comprising a first end and a second end, wherein said tensionable member is attached to a tensioner member, wherein said tensionable member is slideably attached to said frame, wherein said tensionable member forms an endless loop;
wherein said tensionable member is configured to form a loop around a subject's torso generally where the subject's neck and trapezius muscle meet;
wherein from said loop a first segment of said tensionable member is configured to traverse the ventral side of a subject's torso, wherein a second segment of said tensionable member is configured to traverse the dorsal side of a subject's torso, wherein said tensionable member is configured to form a first lateral side loop around a subject's first lateral side inferior to a subject's first arm;
wherein a third segment of said tensionable member is configured to traverse the dorsal side of a subject's torso from said first lateral side loop and a fourth segment of said tensionable member is configured to traverse the ventral side of a subject's torso from said first lateral side loop, wherein said third segment and said forth segment are configured to meet to form a second lateral side loop around the subject's body at an opposite lateral side of said subject's body from said first lateral side loop, wherein said tensionable member is configured to apply lateral force to said subject's body at each of said loops, wherein said tensioner member is configured to adjust the lateral force applied by said tensionable member by applying tension to said tensionable member;
a neck member, wherein said neck member is configured to form a rigid loop around said subject's torso proximate to where said subject's neck and trapezius muscle meet, wherein said neck member is configured such that said tensionable member applies force to said neck member to apply force to said subject's torso;
wherein said neck member comprises a rigid neck member having a length, wherein said rigid neck member comprises cable guides, wherein said tensionable member comprises a cable, wherein said cable travels through said cable guides along said length of said neck member such that said neck member and said cable are configured to form a loop around a subject's neck such that said neck member is between said cable and a subject's neck, wherein said cable is configured to impart force onto said rigid neck member and to said subject's neck.

10. A spinal deformity treatment device for treating a spinal deformity of a human torso, comprising:
a frame adapted to be worn on a subject's torso;
a tensionable member slideably attached to said frame and configured to apply a generally lateral force to a subject's torso at three locations on a subject's torso, wherein said three locations are at a first location generally where a subject's neck and trapezius muscle meet, at a second location on a subject's torso inferior to a subject's first arm and on an opposite lateral side to said first location, and at a third location on said subject's torso in a location inferior to a subject's second arm and on a lateral side of the subject's body opposite from said second location;
a tensioner member, wherein said tensioner member is configured to apply tension to said tensionable member;
wherein said tensioner member comprises an internal winding mechanism.

* * * * *